(12) United States Patent
Geay et al.

(10) Patent No.: US 6,242,742 B1
(45) Date of Patent: Jun. 5, 2001

(54) ROTATING ARTICULATION FOR A TRANSMISSION ATTENUATION CORRECTION DEVICE

(75) Inventors: Jean-Claude Geay, Montign y le Bretonneux; Jean Treillet, Boulogne Billancourt; Bernard Beaumesnil, Le Mans, all of (FR)

(73) Assignee: SMV International, Buc (FR)

( * ) Notice: Subject to any disclaimer, the term of this patent is extended or adjusted under 35 U.S.C. 154(b) by 0 days.

(21) Appl. No.: 09/227,836

(22) Filed: Jan. 11, 1999

(30) Foreign Application Priority Data

Jan. 16, 1998 (FR) .................................................. 98 00448

(51) Int. Cl.⁷ .................................................. G01T 1/161
(52) U.S. Cl. ......................................................... 250/363.04
(58) Field of Search ........................ 250/363.08, 363.05, 250/363.04

(56) References Cited

U.S. PATENT DOCUMENTS

| 5,552,606 | 9/1996 | Jones et al. . |
| 5,576,545 | * 11/1996 | Stoub et al. ..................... 250/363.04 |
| 5,752,916 | 5/1998 | Guerard et al. . |

FOREIGN PATENT DOCUMENTS 2736163   1/1997   (FR) .

* cited by examiner

*Primary Examiner*—Constatine Hannaher
(74) *Attorney, Agent, or Firm*—Connolly Bove Lodge & Hutz

(57) ABSTRACT

An articulation system that allows for the rotation of a TAC device of a dual detector scintigraphy camera in two successive positions, perpendicular and opposite, in order to make it possible to use the TAC device either with perpendicular detectors or with parallel detectors. This articulation system contains a joint face at a 45° angle in relation to the longitudinal axis of a support so that the TAC device can take on two positions, perpendicular and opposite, where passage from one position to the other is obtained by a 180° rotation in relation to the axis of this joint face.

9 Claims, 4 Drawing Sheets

ROTATING ARTICULATION FOR A TRANSMISSION ATTENUATION CORRECTION DEVICE

FIELD OF THE INVENTION

This invention relates to the variable angulation dual detector scintigraphy cameras and, in particular to those cameras that allow for the rotation of a transmission attenuation correction device.

BACKGROUND OF THE INVENTION

In this type of camera, the detectors may be either perpendicular for the acquisition of images of certain organs in a 90° tomography, or face to face for the acquisition of the image of the skeletal system on the entire body or 180° tomography.

These cameras may be equipped with one or two TAC (Transmission attenuation correction) devices. The device contains a known radioactive source that emits gamma energy rays; these rays sweep the active surface of the detector through the body of the patient. The attenuation of energy caused by the patient's body is measured in this detector. This measuring results in information that, when treated appropriately, makes it possible to correct the attenuation of the photon energy emitted by the irradiated organ and therefore to obtain a more detailed image.

The radioactive source is a linear rod in a radiation-proof chamber that is however provided with a rectilinear slot through which the radiation is transmitted in the direction of the detector. This slot must be perfectly closed when the TAC device is not in use. Usually, the closing is controlled mechanically and must be totally secured. The TAC device moves parallel to itself in a plane that is parallel to the detector's detection surface.

As it now stands in the technique, the TAC device is only used for certain image acquisitions and in particular for the 90° tomography, meaning when the detectors are perpendicular. In other cases, in particular for the image acquisition using two parallel detectors facing each other, the TAC device is not rotated to operate.

BRIEF DESCRIPTION OF THE INVENTION

This invention solves this inconvenience by allowing for the use of the TAC device in all three types of configuration mentioned above (90° and 180° tomography, entire body).

It consists of an adjustable articulation made up of a joint face at a 45° angle in relation to the longitudinal axis of the TAC device so that it can take two perpendicular and opposite positions and that passing from one position to the other gives a 180° rotation in relation to the axis of this joint face.

The two positions are indexed by dowels or alignment pins that are diametrically opposite and fit into holes on the opposite part.

One of the two parts of the articulation holds a flanged ring that rotates with the other part and is fitted with screws that can tighten these two parts against each other.

The transmission of the isolation control movement of the source takes place thanks to a set of pinions located in the center part of the joint face.

During the rotation of the chamber that carries the source around the axis, the pinions are pulled apart so that the source can stay isolated and, after being repositioned, said pinions are remeshed while maintaining the isolation of the source.

The driving pinion and the driven pinion are both braced conical pinions turned in such a way that the space along the axis of the joint face causes their disconnection.

The articulation can be either a part that is integrated in the support, a removable part inserted between the two parts of the support, or a removable part inserted between the support and a cassette carrying the source.

At one end of the removable part that is inserted between the support and a cassette carrying the source, is the male part and at the other end is the female part of an assembly that is identical to the secured assembly of the cassette on the support.

The characteristics and advantages of the invention will appear through the following description of a non restrictive example in reference to the attached drawings where

DETAILED DESCRIPTION

Figure 1:
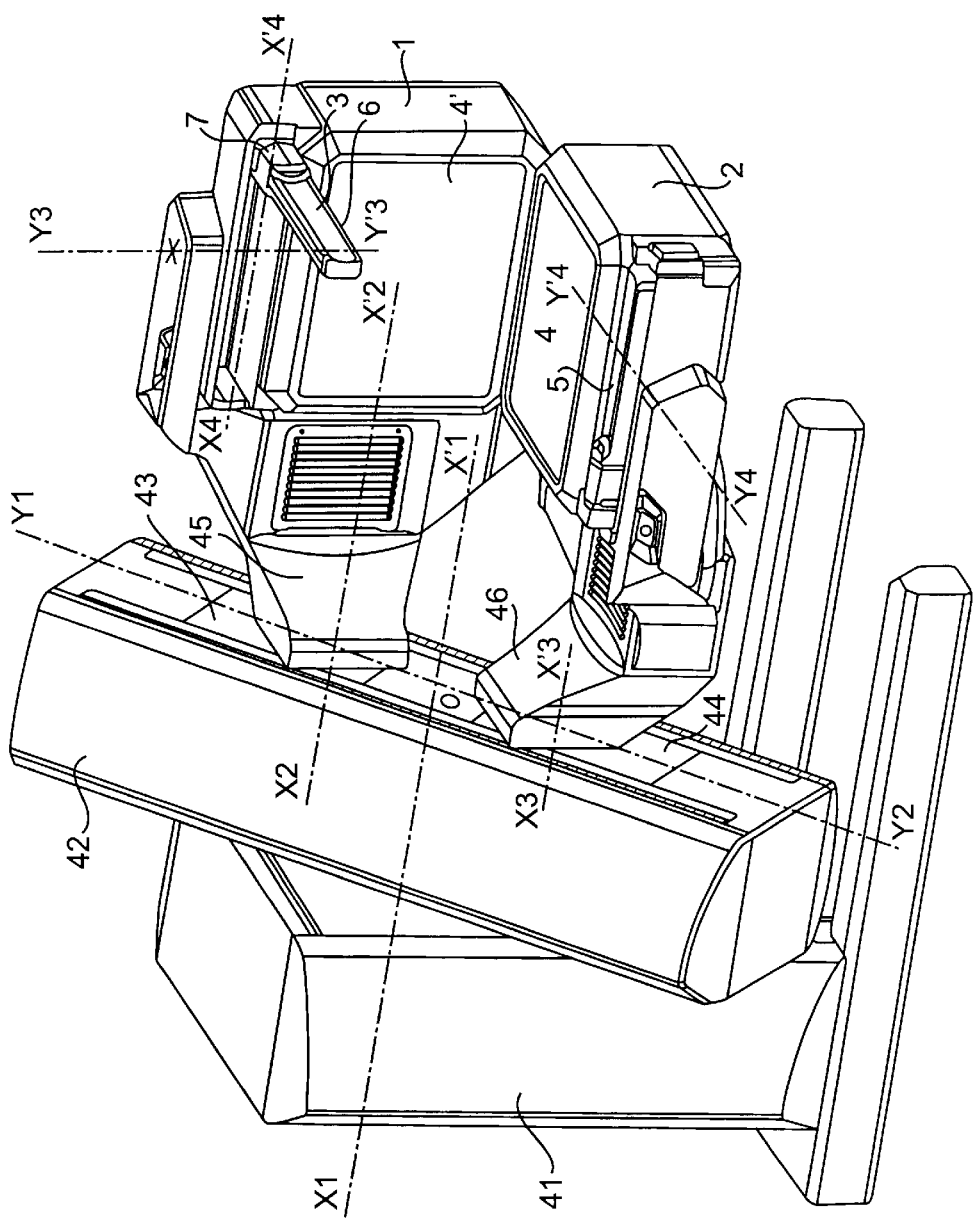
FIG. 1 represents an overall view of an open stand double headed camera, where both detectors are placed at a 90° angle and are each fitted with a TAC device, one in operating position and the other in resting position.

In FIG. 1, the gamma camera consists of a stand (41) that supports a revolving base (42) that holds carriages (43) (44) each respectively fitted with two detector (1) (2) supports (45) (46) whose detection surfaces are referenced (4) (4').

The stand (42) revolves around the axis X1 X'1;

The carriages (43) and (44) move linearly following the direction OY1 OY2;

The detector supports turn respectively around the axes X2 X'2 and X3 X'3;

The detectors turn respectively around axes Y3 Y'3 and Y4 Y'4.

Thus, we see that the detectors can take any position within a certain space and in particular be perpendicular as illustrated in the figure or parallel facing each other, etc.

In FIG. 1, the camera's two detectors (1) and (2) are represented as perpendicular, where a first TAC device (3) is positioned so that its emitting face (6) radiates face (4) of the detector (2) whereas a second TAC device (5) is in resting position. The TAC device (3) moves according to the axis X4X'4 so that the gamma rays emitted sweep the entire surface (4) of the detector (2).

Figure 2:
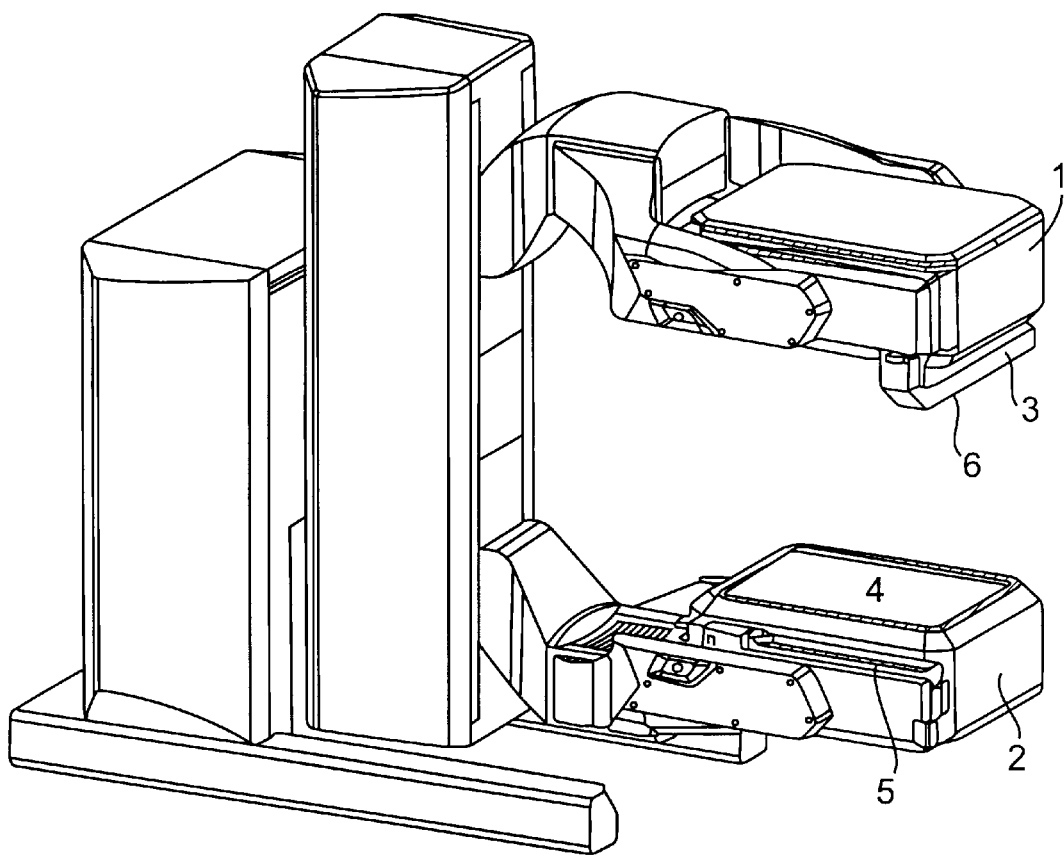
FIG. 2 represents the same camera with the two detectors facing each other, where one is equipped with a TAC device that faces the other detector.

In FIG. 2, the detectors (1) and (2) face each other, the TAC device (3) is folded at a 90° angle from its original position and has been rotated 180° on its axis so that its emitting face (6) is turned toward the face (4) of the detector (2). In this configuration, the TAC device (5) remains in the resting position.

This double modification of orientation corresponds to a simple 180° rotation around the axis X'X (FIG. 3) of a joint face positioned at a 45° angle in relation to the principal axis AP of the first TAC device 3.

Figure 3:
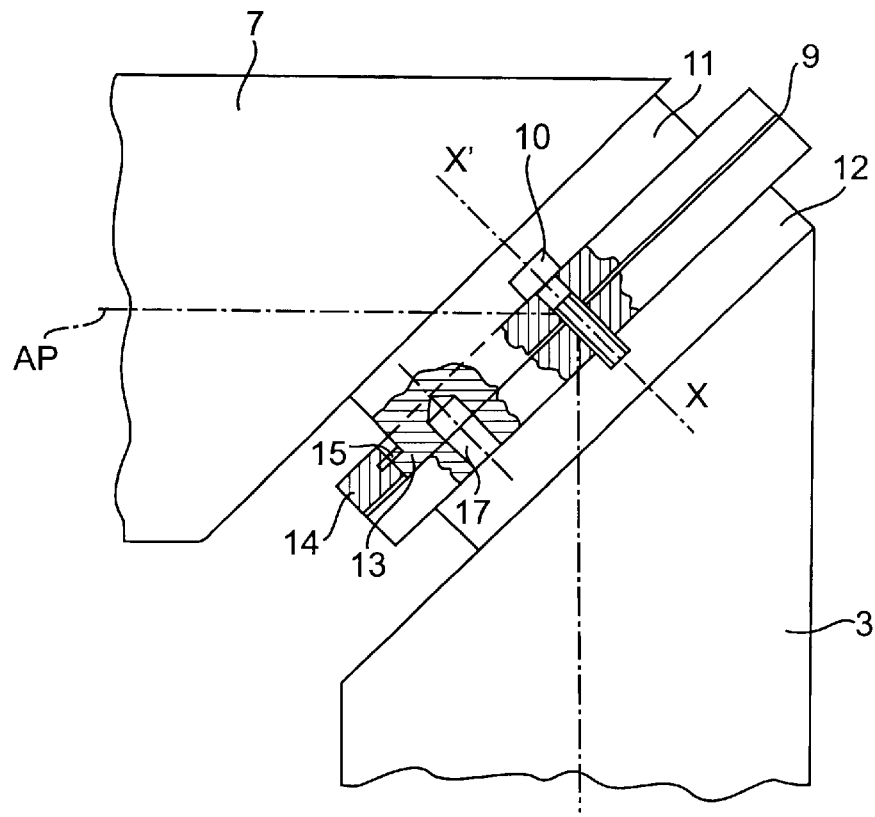
FIG. 3 illustrates an example of the articulation as set forth in the invention in its "right angle" placement.
Figure 4:
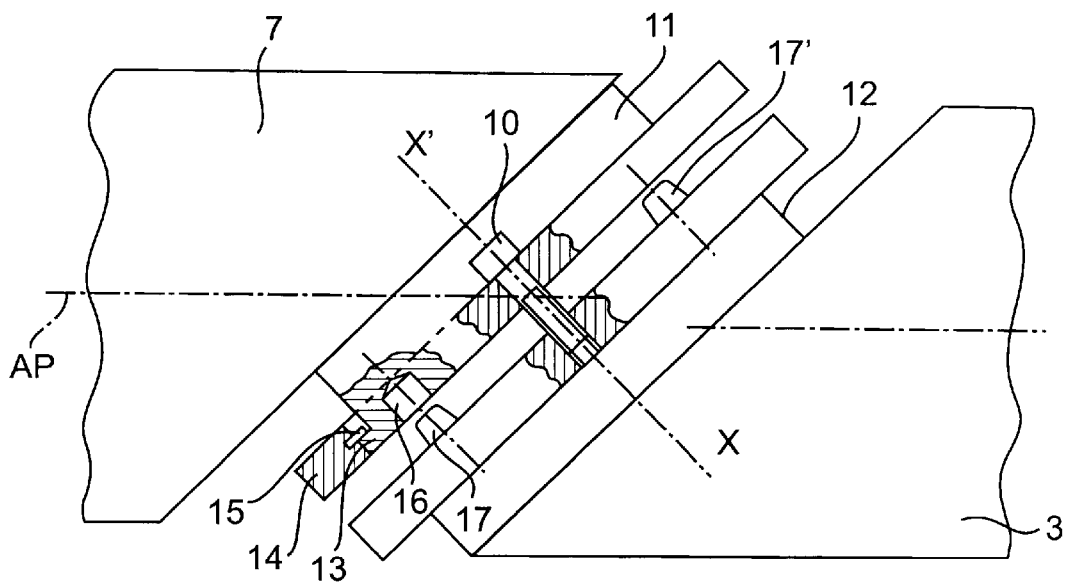
FIG. 4 is a view of the same example in an "in line" placement prior to the tightening of the mounting screws.

FIGS. 3 and 4, which illustrate a non-restrictive example, use the support (7) and the actual TAC device (3); these two parts are linked by a joint face at 45° (9) and assembled by two screws (10). The two parts (7) and (3) have an ordinary profile, but it is always possible to include a cylindrical part (11) (12) in the 45° section. The cylinder (11) ends in a shoulder (13) around which there is a ring (14) flanged by a snap ring (15). There are at least two holes in the joint face (9) of which only one (16) is represented in FIGS. 3 and 4, these holes, diametrically opposite, are intended to hold the centering dowels (17) (17'). To go from the square angle position (FIG. 3) to the aligned position (FIG. 4), all that is needed is to loosen the screws (10) until the dowels (17) (17') are cleared from their seating (16) (16') and to rotate the TAC device (3) 180°, which causes the ring (14) to turn since it is linked to the TAC (3) by the screws (10) and, possibly, by other guides that are not represented. The dowels (17)(17') then find the opposite seating and all that remains to be done is to retighten the screws (10).

Figure 5:
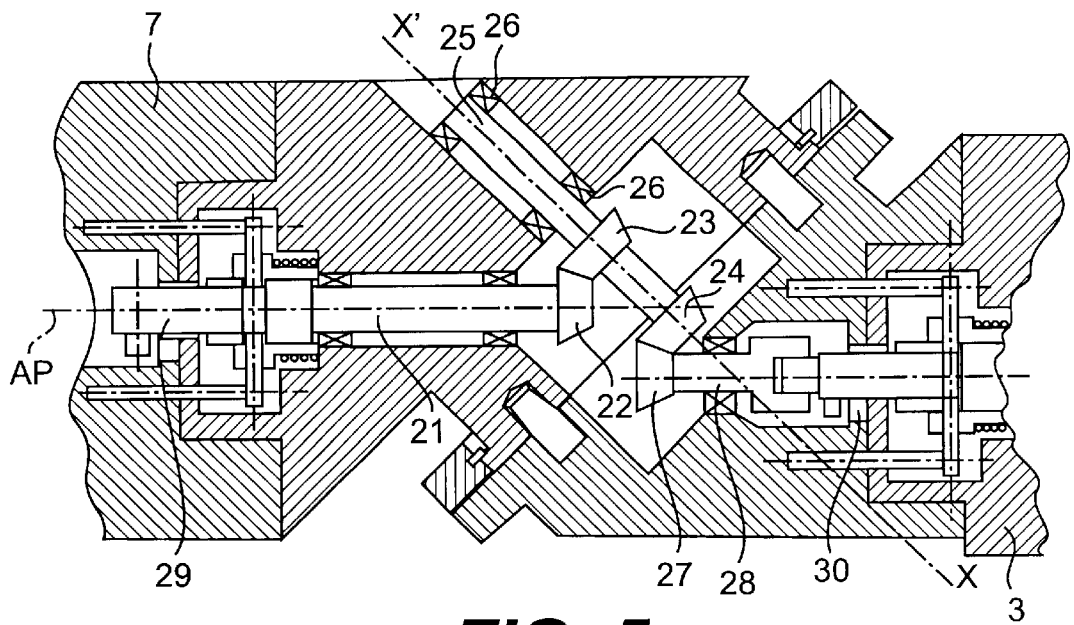
FIG. 5 is a diametric sectional view of an example of the articulation represented in FIG. 3.

When the isolation mechanism of the source is located on the TAC device (3), the joint face is simple and only holds in its center the contacts needed to bring the electrical current to the mechanism. If, on the other hand, the mechanism is placed on the support side (7), the opening and closing motion of the source must be transmitted through the joint face while maintaining the closed position, therefore radiation opaque, during the 180° rotation around the X'X axis. With this end in view, we can imagine various solutions related to the non-restrictive example represented in FIGS. 5 and 6.

Figure 6:
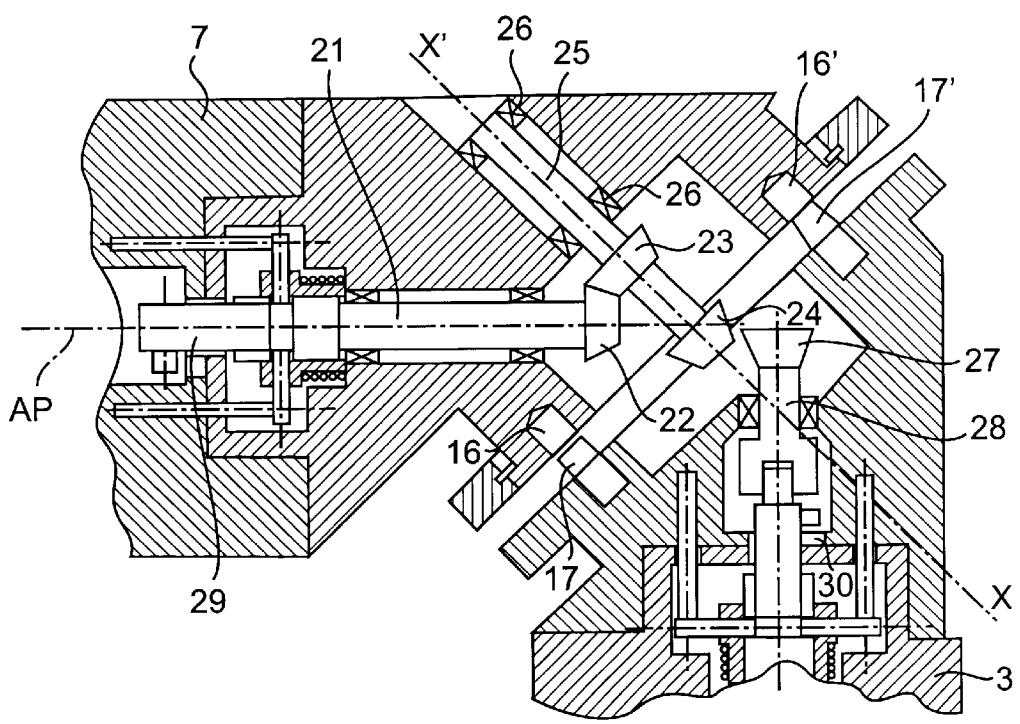
FIG. 6 is a diametric sectional view of the same example after a 180° rotation and prior to the tightening of the mounting screws.

The isolation mechanism of the source transmits the motion through the shaft (21) which ends in a conic pinion (22); the latter meshes with the second conic pinion (23) integral with a third conic pinion (24) by means of a shaft (25) centered on the rotation axis X'X and which revolves on a bearing (26) of the support (7). On the other side of the joint face, a pinion (27) integral with a shaft (28) meshes with the pinion (24); the shafts (21) and (28) are either parallel and slightly off set (FIG. 5) or perpendicular (FIG. 6).

When the screws (10) are loosened, the two parts (7) and (3) move apart following the X'X axis until the dowels (17) (17') are removed from their seating (16) (16') which causes the pinion (27) to pull away. It can be advantageous to force this separation using a spring device that is not represented. Thus, after the 180° rotation during which the pinion (27) is disengaged, and therefore has no effect on the isolation of the source, said pinion is then ready to mesh as represented in FIG. 6. The dowels (17)(17') place themselves in front of the seating that is opposite to the preceding seating and all that remains to be done is to tighten the screws (10) to once again make the TAC device operational.

This articulation device can be integral with the support (7), integral with the TAC device (3) or independent in order to give an option. This interface would then consists at one extremity of the male part (29) and at the other extremity of the female part (30) of the secured assembly system provided for between the support and the cassette in order to use the TAC device with or without the articulation.

This polyvalent use of the TAC device makes it possible to improve the quality of the images for all acquisitions to the benefit of a better diagnostic in nuclear medicine.

What is claimed is:

1. A rotating articulation for a transmission attenuation correction device (TAC device), mounted on a dual detector scintigraphy camera with a variable angulation, the TAC device holding a linear radioactive source chamber movable in translation parallel to a detection surface of a detector, the rotating articulation comprising:
    a support having a principal axis;
    a joint face located between the support and the TAC device and positioned at a 45° angle in relation to the principal axis of the support, so that the TAC device may selectively assume one of two positions, namely perpendicular or aligned with the support, where the transition from one position to the other is obtained by a 180° rotation of the rotating articulation about an axis perpendicular to the joint face.

2. An articulation as set forth in claim 1, wherein the two positions are indexed by diametrically opposite centering dowels that selectively penetrate holes in the joint face.

3. An articulation as set forth in claim 1 together with a flanged ring connected to a preselected one of the support or TAC device, adjacent the joint face, and fitted with screws that are accessible from an exterior point for fastening the support and TAC device together.

4. An articulation as set forth in claim 1 further comprising a gear drive extending through the joint face for transmitting rotation of the TAC device.

5. An articulation as set forth in claim 4 wherein, during the rotation of the TAD device, gears of the gear train become disengaged to isolate the radioactive source.

6. An articulation as set forth in claim 4 wherein the gear drive further comprises spaced driving and driven beveled gears linked by coaxially positioned intermediary beveled gears respectively meshing with the driving and driven gears.

7. An articulation as set forth in claim 6 wherein separation of the TAD device from the support, along the axis perpendicular to the joint face, causes disengagement of the gear drive.

8. An articulation as set forth in claim 1 wherein the TAD device may be: integrated in the support, removably inserted between two components of the support, or removably inserted between the support and a cassette bearing the support.

9. An articulation as set forth in claim 8, further comprising a removable part inserted between the support and a cassette containing the source, and further wherein at one extremity the articulation has a male member, and at an opposite extremity the articulation has a female member of an assembly that is identical to a secured assembly of the cassette bearing the support.

* * * * *